United States Patent [19]
Collins

[11] Patent Number: 5,116,307
[45] Date of Patent: May 26, 1992

[54] METHOD AND SYSTEM FOR TREATMENT OF AIDS

[76] Inventor: Harvey T. Collins, 1486 E. 56th St., Chicago, Ill. 60637

[21] Appl. No.: 549,961

[22] Filed: Jul. 9, 1990

[51] Int. Cl.⁵ ............................................. A61M 37/00
[52] U.S. Cl. .......................................... 604/4; 604/5; 604/6; 210/264
[58] Field of Search ...................................... 604/4-6, 604/317-320; 210/764

[56] References Cited

U.S. PATENT DOCUMENTS

| | | | |
|---|---|---|---|
| 4,634,447 | 1/1987 | Isono et al. | 623/66 |
| 4,838,852 | 6/1989 | Edelson et al. | 604/4 |
| 4,855,064 | 8/1989 | Schlein | 604/4 X |
| 4,895,558 | 1/1990 | Cham | 604/4 |
| 4,915,683 | 4/1990 | Sieber | 604/4 |
| 4,950,225 | 8/1990 | Davidner et al. | 604/4 |
| 4,960,408 | 10/1990 | Klainer et al. | 604/4 |

*Primary Examiner*—Robert A. Hafer
*Assistant Examiner*—Kerry Owens
*Attorney, Agent, or Firm*—Thomas R. Vigil

[57] ABSTRACT

The method and system for the extracorporeal or extravascular treatment of blood employs diethyl ether for killing HIV cells in the blood. In practicing the method with the system, blood is withdrawn from one arm of a patient through a tubing to a container, e.g. a syringe barrel, where the blood is exposed to vaporized diethyl ether, which has been vaporized by heating, thereby to enable the diethyl ether to strip the viral envelope away from HIV cells attached to macrophages and dissolve the lipid layers thereof thereby to kill the HIV cells. The blood with ether is then passed through a manifold where a vacuum is drawn on the blood to remove most of the ether from the blood. The treated blood is then returned by a tubing and needle to the other arm of the patient. A blood thinner or anticoagulant preferably is given first to the patient orally or intravenously. Also preferably an electrical pulse is supplied to the arm of the patient upstream of the point where blood is removed for the purpose of inhibiting the clumping of the infected white blood cells to non-infected white blood cells thereby to force the HIV cells, or macrophages containing HIV cells, into the blood stream so that they are more vulnerable to being destroyed by the ether. Further, if desired, new blood can be introduced into the patient's other arm with the returned treated blood to provide "make up" blood cells for blood cells that may have been destroyed by the ether.

6 Claims, 1 Drawing Sheet

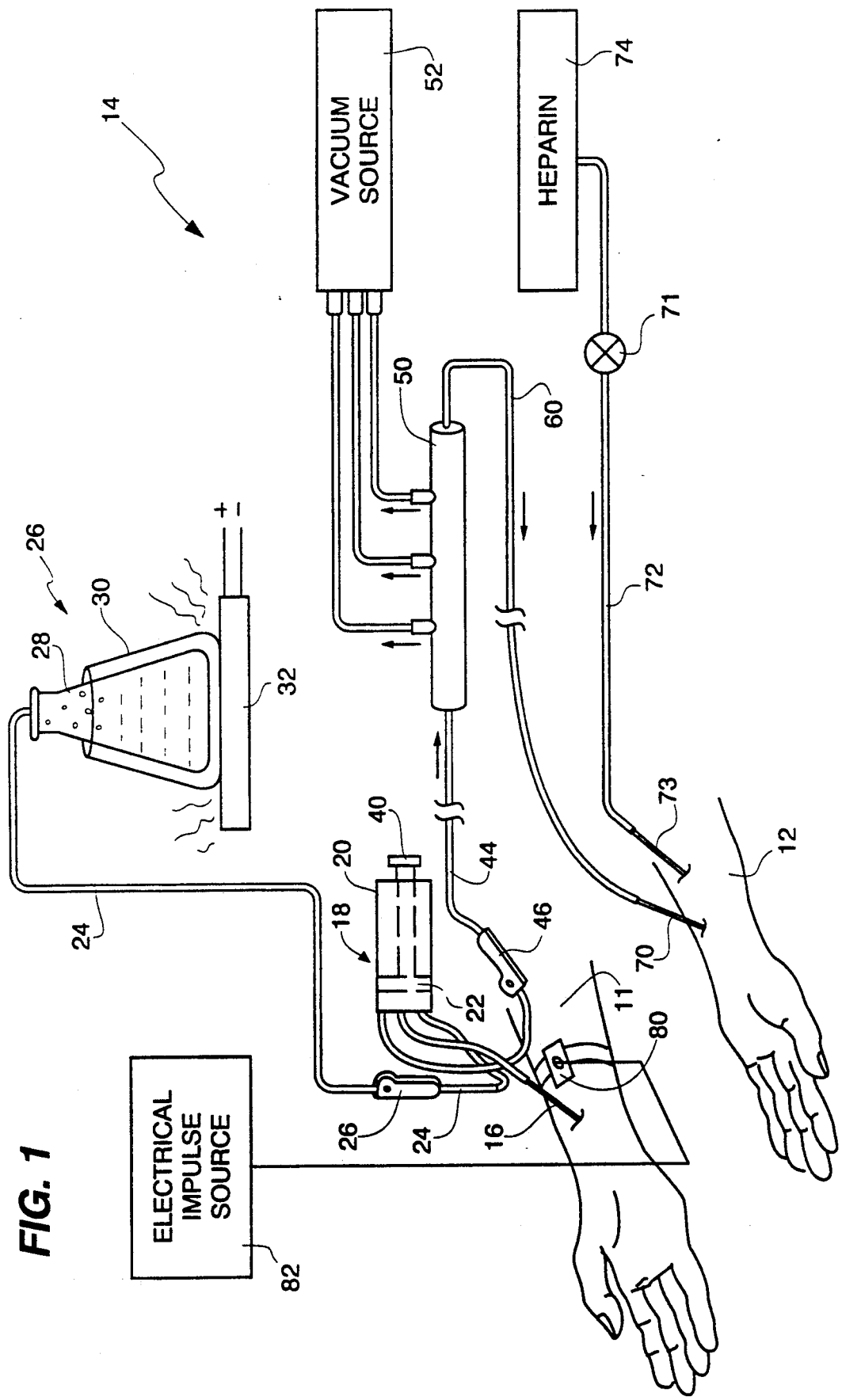

METHOD AND SYSTEM FOR TREATMENT OF AIDS

BACKGROUND OF THE INVENTION

1. Field of the Invention

The present invention relates to the extravascular treatment of blood cells with diethyl ether to strip away the viral envelope of an HIV cell attached to a macrophage and dissolve the lipid layer of the HIV cell thereby to destroy the HIV cell.

2. Description of the Related Art including Information disclosed under 37 CFR §§1.97-1.99

Heretofore the extravascular or extracorporeal treatment of blood cells for treating blood for removing, altering, effecting or killing a substance carried in the blood for effecting a therapeutic procedure intended to ameliorate a condition a patient is suffering from, have been proposed.

For example, the Edelson U.S. Pat. No. 4,683,689 teaches a method and system for externally treating the blood of a cancer patient with radiation for reducing the population of undesirable autoreactive antibodies; and the Hayden U.S. Pat. No. 4,820,260 teaches a method and apparatus for extravascular treatment of red blood cells with ultrasound to inactivate sodium, potassium. ATPase enzyme.

The method and system of the present invention differ from the method and apparatus referred to above by providing for the treatment of a patient's blood with diethyl ether vapor in an extravascular or extracaporeal treatment procedure for the purpose of killing HIV cells attached to macrophages in the blood.

SUMMARY OF THE INVENTION

According to the teachings of the present invention, there is provided a method and system for the extracaporeal or extravascular treatment of blood for killing HIV cells in the blood. In practicing the method of the present invention with the system of the invention, blood is withdrawn from the right arm of a patient through a tubing to a container, e.g. a syringe barrel, where the blood is exposed to vaporized diethyl ether, which has been vaporized by heating, thereby to enable the diethyl ether to strip the viral envelope away from HIV cells attached to macrophages and thereby kill the HIV cells. The blood with ether is then passed through a manifold where a vacuum is drawn on the blood to remove most of the ether from the blood. The treated blood is then returned by a tubing and needle to the other arm of the patient.

A blood thinner or anticoagulant preferably is given to the patient orally or intravenously prior to practicing the method.

Also preferably an electrical pulse is supplied to the arm of the patient upstream of the point where blood is removed for the purpose of inhibiting the clumping of the infected white blood cells to noninfected white blood cells thereby to force the HIV cells, or macrophages containing HIV cells, into the blood stream so that they are more vulnerable to being destroyed by the ether.

Further, if desired, new blood can be introduced into the patient's left arm with the returned treated blood to provide "make up" blood cells for blood cells that may have been destroyed by the ether.

BRIEF DESCRIPTION OF THE DRAWINGS

The single FIGURE, FIG. 1 of the drawings is a block schematic diagram of a system for removing blood from an aids patient, for treating the blood with ether to kill HIV infected cells with ether and for returning the treated blood to the patient.

DESCRIPTION OF THE PREFERRED EMBODIMENTS

Research on the aids (HIV) virus seems to link the virus to the destruction of the macrophage before the T-4 cells can alert the macrophages to marshal the eight components of the immune system to react to an HIV infection.

The damaged or infected macrophages then cannot secrete the chemicals needed to prevent systematic damage to the brain and other organs.

The method and system of the present invention are designed to destroy HIV cells by contacting the virus cells with diethyl ether even when the virus cells lie dormant in the macrophages and only a few T-4 cells are infected. The virus is destroyed in vitro and the treated blood is transfused into a patients body.

The human body can tolerate 7% v/v of ether. Accordingly a vacuum is drawn on the treated blood before it is returned to the body to reduce the level of ether to a level well below 7%.

Furthermore, the small amount of ether that is still present in the treated blood may be effective in killing the virus in vivo.

Referring to FIG. 1, there is shown therein the left and right arms 11, 12 of an aids patient having the system 14 of the present invention connected thereto.

The system 14 includes a hypodermic needle 16 which is inserted into a vein in the right arm 11. The hypodermic needle 16 extends to a syringe 18 including a syringe barrel on cylinder 20 having a plunger 22 therein.

The cylinder 20 has connected thereto a tubing 24 having a flow restrictor 26 thereon. The tubing 24 extends to a source 26 of diethyl ether which in the illustrated embodiment is realized by a beaker or flask 28 of ether having a heating mantle 30 and being positioned on a heating plate 32. A heat control knob (not shown) for controlling the boiling of the ether is provided.

Vaporizes ether is supplied from the flask 28 to the syringe cylinder 20 and the amount of ether is controlled by the flow restrictor 26.

A knob 40 connected to the plunger 22 can be used for educing blood from the patient and at the same time for drawing ether from the flask 28 through suitable one-way check valves (not shown) in the connection of the needle 16 to the cylinder 20 and in the connection of the tubing 22 to the cylinder 20.

After a suitable amount of blood and ether have been drawn into the syringe cylinder 20, the blood mixed with ether is drawn out through a tubing connection 42 having a one-way check valve (not shown) therein to a tubing 44 having a flow restrictor 40 mounted thereon. The tubing 44 then extends to a manifold 50 to which a source of vacuum or vacuum pump 52 is connected for placing the blood in the manifold under a vacuum to draw off most of the ether before the blood is returned to the patient.

A return tubing 60 then extends from the manifold 50 to a needle 70 which is inserted into the left arm of the patient for return of the treated blood to the body.

As shown, a small amount of heparin can be supplied through a valve 71, tubing 72 and needle 73 from a source 74 to a vein in the left arm 12 in the patient to inhibit clotting.

Alternatively, an oral anti-coagulant of heparin or aspirin can be supplied to the patient prior to treatment, for inhibiting clotting, instead of the vascular injection of heparin.

Also alternatively, instead of utilizing a syringe 18, the needle 16 injected in the right arm 11 can be simply connected to a combining chamber cylinder 20 to which the ether tubing 22 is connected so that the blood can freely flow out of the patient's arm into the ether/blood combining chamber 20 and then into the tubing 44 leading to the manifold 50.

In addition, if desired, a pump, e.g., a peristaltic pump, (not shown) can be mounted on the return tubing 60 to assist the flow of blood back to the patient.

Preferably, an electrode 80 is attached to the right arm 11 of the patient near the wrist and an indifferent electrode (not shown) connected to the body whereby small voltage electrical pulses from an electrical impulse source 82 can be intermittently supplied to the body.

The electrical pulses increase the effectiveness of the ether in stripping away of the viral envelope of the HIV and the dissolution of the lipid layer common to all viruses. In particular the electrical pulses inhibit the clumping of the infected white blood cells to the non-infected blood cells to force the virus cells, on independent cells having the virus into the blood stream thereby to render them more vulnerable to being destroyed by the ether.

Also preferably new blood is transfused to the patient with the treated blood to replenish healthy blood cells that may have been killed off by the ether.

In practicing the method of the present invention utilizing the system 10 described above, the blood is maintained in contact with the ether for approximately one half minute before the ether is drawn off by the vacuum pump.

The extracorporeal or extravascular treatment of the blood with ether is carried out for different lengths of times, e.g., 15 minutes to 2 hours, at different time intervals, e.g., once a week to up to 3 times a day, depending upon the patient's body weight/blood volume, stage of the virus infection and the acuteness of the virus infection.

It is believed that after clinical tests have been conducted with the method of the present invention, more specific parameters will be established for the frequency of treatment with the method of the present invention for treating HIV infected patients.

Also, it is to be understood that the method and system of the present invention can be utilized for treating other viruses such as the Epstein Barr virus.

From the foregoing description it will be apparent that the method and system of the present invention provides for the extracorporeal or extravascular treatment of blood cells infected with HIV cells by exposing them to diethyl ether thereby to strip away the viral envelope and dissolve the lipid layer killing the virus to control or manage the HIV infection.

Further from the foregoing description, it will be apparent that modifications can be made to the method and system of the present invention without departing from the teachings of the invention. Accordingly, the scope of the present invention is only to be limited as necessitated by the accompanying claims.

I claim:

1. A method for the extracorporeal or extravascular treatment of blood for killing virus cells in the blood comprising the steps of:
    withdrawing blood from one arm of a patient;
    passing the withdrawn blood through a container;
    exposing the blood in the container to vaporized diethyl ether, which has been vaporized by heating, thereby to enable the diethyl ether to strip the viral envelope away from the virus cells and dissolve the lipid layers of same in the blood thereby to kill the virus cells;
    passing the blood through a manifold;
    drawing a vacuum on the blood in the manifold to remove most of the ether from the blood; and
    returning the treated blood to the other arm of the patient.

2. The method of claim 1 including the first step of supplying a blood thinner or anticoagulant to the patient.

3. The method of claim 1 including the step of supplying an electrical pulse to the arm of the patient upstream of the point where blood is removed for the purpose of inhibiting the clumping of infected white blood cells to non-infected white blood cells thereby to force HIV cells, or macrophages containing HIV cells, into the blood stream so that they are more vulnerable to being destroyed by the ether.

4. The method of claim 1 including the step of supplying new blood to the patient's arm with the returned treated blood to provide the patient with "make up" blood cells for blood cells that may have been destroyed by the ether.

5. A system for the extracorporeal or extravascular treatment of blood for killing virus cells in the blood comprising:
    means for withdrawing blood from one arm of a patient;
    a container;
    means for passing the withdrawn blood through said container;
    means for exposing the blood in said container to vaporized diethyl ether, which as been vaporized by heating, thereby to enable the diethyl ether to strip the viral envelope away from the virus cells and dissolve the lipid layers of same in the blood thereby to kill the virus cells;
    a manifold;
    means for passing the blood through said manifold;
    means for drawing a vacuum on the blood in said manifold to remove most of the ether from the blood; and
    means for returning the treated blood to the other arm of the patient.

6. The apparatus of claim 5 including means for supplying an electrical pulse to the arm of the patient upstream of the point where blood is removed for the purpose of inhibiting the clumping of infected white blood cells to noninfected white blood cells thereby to force HIV cells, or macrophages containing HIV cells, into the blood stream so that they are more vulnerable to being destroyed by the ether.

* * * * *

UNITED STATES PATENT AND TRADEMARK OFFICE
CERTIFICATE OF CORRECTION

PATENT NO. : 5,116,307

DATED : May 26, 1992

INVENTOR(S) : Harvey T. Collins

It is certified that error appears in the above-identified patent and that said Letters Patent is hereby corrected as shown below:

Abstract, line 1 "HIV cells" should be --HIV virus--.

Abstract, line 7 "HIV cells" should be --HIV virus--.

Abstract, line 8 "HIV cells." should be --HIV virus.--.

Abstract, line 19 "HIV cells," should be --HIV virus,--.

Abstract, line 20 "HIV cells," should be --HIV virus,--.

Column 1, line 9 "HIV cells" should be --HIV virus--.

Column 1, line 11 "HIV cells" should be --HIV virus--.

Column 1, line 12 "HIV cells" should be --HIV virus--.

Column 1, line 34 "HIV cells" should be --HIV virus--.

Column 1, line 40 "HIV cells" should be --HIV virus--.

Column 1, line 47 "HIV cells" should be --HIV virus--.

Column 1, line 48 "HIV cells" should be --HIV virus--.

Column 1, line 61 "HIV cells" should be --HIV virus--.

Column 1, line 62 "HIV cells" should be --HIV virus--.

Column 2, line 6 "HIV infected cells" should be --HIV virus in the cells--.

Column 2, line 20 "HIV cell" should be --HIV virus--.

UNITED STATES PATENT AND TRADEMARK OFFICE
CERTIFICATE OF CORRECTION

PATENT NO. : 5,116,307            Page 2 of 2

DATED : May 26, 1992

INVENTOR(S) : Harvey T. Collins

It is certified that error appears in the above-identified patent and that said Letters Patent is hereby corrected as shown below:

Column 2, line 47 "Vaporizes" should be --Vaporized--.

Column 3, line 13 "b-lood" should be --blood--.

Column 3, line 60 "HIV cells" should be --HIV virus--.

Column 4, line 29 "cells" should be --virus--.

Column 4, line 29 "HIV cells," should be --HIV virus,--.

Column 4, line 46 "which as" should be "which has--.

Column 4, line 63 "HIV cells," should be --HIV virus,--.

Column 4, line 63 "HIV cells," should be --HIV virus,--.

Signed and Sealed this

Twenty-second Day of March, 1994

*Attest:*

BRUCE LEHMAN

*Attesting Officer*     *Commissioner of Patents and Trademarks*